US011872764B2

(12) United States Patent
Rajapakse

(10) Patent No.: US 11,872,764 B2
(45) Date of Patent: Jan. 16, 2024

(54) THREE-DIMENSIONAL PRINTING FROM IMAGES

(71) Applicant: The Trustees of the University of Pennsylvania, Philadelphia, PA (US)

(72) Inventor: Chamith Sudesh Rajapakse, Cherry Hill, NJ (US)

(73) Assignee: THE TRUSTEES OF THE UNIVERISTY OF PENNSYLVANIA, Philadelphia, PA (US)

( * ) Notice: Subject to any disclaimer, the term of this patent is extended or adjusted under 35 U.S.C. 154(b) by 181 days.

(21) Appl. No.: 16/768,645

(22) PCT Filed: Dec. 5, 2018

(86) PCT No.: PCT/US2018/064134
§ 371 (c)(1),
(2) Date: May 29, 2020

(87) PCT Pub. No.: WO2019/113254
PCT Pub. Date: Jun. 13, 2019

(65) Prior Publication Data
US 2021/0170689 A1 Jun. 10, 2021

Related U.S. Application Data

(60) Provisional application No. 62/595,528, filed on Dec. 6, 2017.

(51) Int. Cl.
*B29C 64/386* (2017.01)
*B33Y 10/00* (2015.01)
(Continued)

(52) U.S. Cl.
CPC .......... *B29C 64/386* (2017.08); *B29C 64/118* (2017.08); *B33Y 10/00* (2014.12);
(Continued)

(58) Field of Classification Search
CPC ......... B33Y 10/00; B33Y 30/00; B33Y 50/00; G06T 11/008; G06T 17/00;
(Continued)

(56) References Cited

U.S. PATENT DOCUMENTS

2013/0194410 A1* 8/2013 Topman .................... G06T 7/44
382/133
2015/0076739 A1 3/2015 Batchelder
(Continued)

OTHER PUBLICATIONS

Tokiwa et al., "Biodegradability of Plastics," International Journal of Molecular Sciences, vol. 10, No. 9, pp. 3722-3742 (2009).
(Continued)

*Primary Examiner* — Ming Wu
(74) *Attorney, Agent, or Firm* — Jenkins, Taylor & Hunt, P.A.

(57) ABSTRACT

Methods, systems, and computer readable media for 3D printing from images, e.g., medical images or images obtained using any appropriate volumetric imaging technology. In some examples, a method includes receiving, from a medical imaging device, a multi-dimensional image of a structure. The method includes, for each two dimensional (2D) slice of the multi-dimensional image, converting, row-by-row for each row of the 2D slice, voxels of the 2D slice into 3D printing instructions for the 2D slice. The method includes 3D printing, by controlling a 3D printing extruder, a physical model based on the structure by 3D printing, slice by slice, each 2D slice using the 3D printing instructions.

18 Claims, 6 Drawing Sheets

(51) Int. Cl.
   *B33Y 30/00*    (2015.01)
   *B33Y 50/00*    (2015.01)
   *G06T 7/11*     (2017.01)
   *G06T 7/149*    (2017.01)
   *B29C 64/118*   (2017.01)
   *G06T 11/00*    (2006.01)
   *G06T 17/00*    (2006.01)
(52) U.S. Cl.
   CPC .............. *B33Y 30/00* (2014.12); *B33Y 50/00* (2014.12); *G06T 7/11* (2017.01); *G06T 7/149* (2017.01); *G06T 11/008* (2013.01); *G06T 17/00* (2013.01); *G06T 2207/10081* (2013.01); *G06T 2207/10088* (2013.01); *G06T 2207/20121* (2013.01); *G06T 2207/30004* (2013.01); *G06T 2211/40* (2013.01)
(58) Field of Classification Search
   CPC . G06T 2207/10081; G06T 2207/10088; G06T 2207/20121; G06T 2207/30004; G06T 2211/40; G06T 7/11; G06T 7/149
   See application file for complete search history.

(56) References Cited

U.S. PATENT DOCUMENTS

| | | | |
|---|---|---|---|
| 2015/0154321 A1* | 6/2015 | Schmidt | B29C 64/40 700/98 |
| 2016/0240003 A1* | 8/2016 | Frayne | B29C 64/364 |
| 2016/0331467 A1 | 11/2016 | Slamin et al. | |
| 2017/0181798 A1 | 6/2017 | Panescu et al. | |
| 2017/0297111 A1* | 10/2017 | Myerberg | B28B 1/001 |
| 2017/0315191 A1* | 11/2017 | Lee | G01R 33/4824 |

OTHER PUBLICATIONS

Grevera et al., "CAVASS: a Computer-Assisted Visualization and Analysis Software System," Journal of Digital Imaging, vol. 20, Suppl 1, pp. 101-118 (2007).

Notification of Transmittal of the International Search Report and the Written Opinion of the International Searching Authority, or the Declaration for International Application No. PCT/US18/64134 (dated Mar. 8, 2019).

* cited by examiner

THREE-DIMENSIONAL PRINTING FROM IMAGES

PRIORITY CLAIM

This application claims the benefit of U.S. Provisional Patent Application Ser. No. 62/595,528, filed Dec. 6, 2017, the disclosure of which is incorporated herein by reference in its entirety.

TECHNICAL FIELD

This specification relates generally to three-dimensional (3D) printing from images, e.g., magnetic resonance (MR) images and computed tomographic (CT) images of anatomical structures.

BACKGROUND

Various imaging technologies allow generation of volumetric computer models that can be 3D printed. However, due to historic reasons, generation of the instruction set understood by 3D printers (e.g., G-Code) requires substantial user interaction and image manipulations. This process can take a significant amount of time depending on the type of images and application. Furthermore, during the conventional image-based G-Code generation process, some anatomical information could be lost due to surface rendition followed by re-slicing.

Accordingly, there exists a need for improved methods for 3D printing from medical images.

SUMMARY

This specification describes methods, systems, and computer readable media for 3D printing from images, e.g., medical images or images obtained using any appropriate volumetric imaging technology. In some examples, a method includes receiving multi-dimensional image(s) of an anatomical structure; for each two dimensional (2D) slice of the original or resampled/processed image(s), converting, row-by-row for each row of the 2D slice, voxels of the 2D slice into 3D printing instructions for the 2D slice; and 3D printing a physical model based on the anatomical structure by 3D printing, slice by slice, each 2D slice using the 3D printing instructions.

The subject matter described herein may be implemented in hardware, software, firmware, or any combination thereof. As such, the terms "function" or "node" as used herein refer to hardware, which may also include software and/or firmware components, for implementing the feature(s) being described. In some exemplary implementations, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

DETAILED DESCRIPTION

Figure 1:
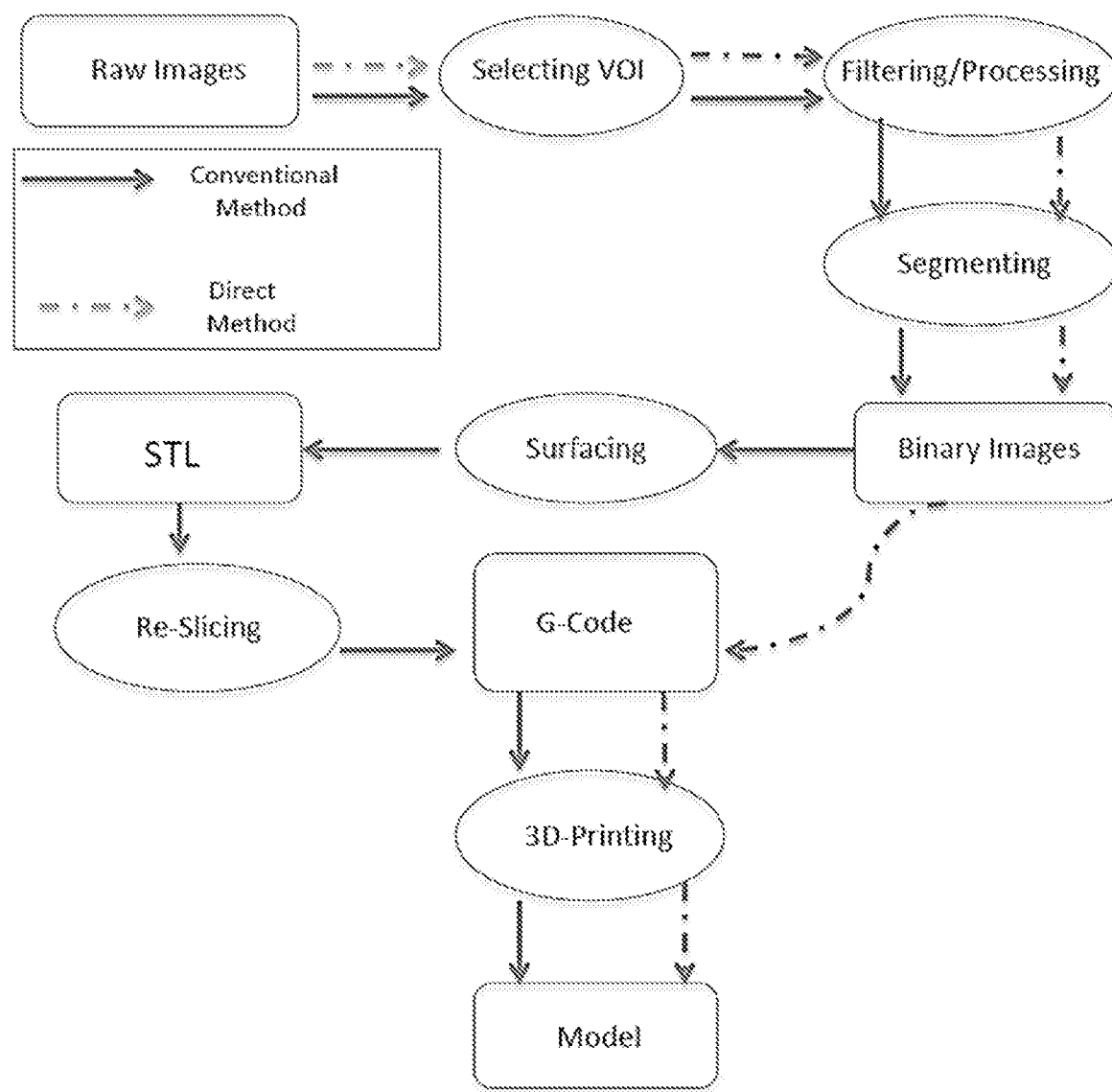
FIG. 1 is a flow chart illustrating methods for 3D printing from medical images.

This specification describes methods, systems, and computer readable media for 3D printing from images. The methods, systems, and computer readable media are described below with reference to a study performed on the methodology.

Bioprinting of tissue has its applications throughout medicine. Recent advances in medical imaging allows the generation of 3-dimensional models that can then be 3D printed. However, the conventional method of converting medical images to 3D printable G-Code instructions has several limitations, namely significant processing time for large, high resolution images, and the loss of microstructural surface information from surface resolution and subsequent reslicing. We have overcome these issues by creating a computer program that skips the intermediate triangularization and reslicing steps and directly converts binary images into G-Code.

In one study, we tested the two methods of G-Code generation on the application of synthetic graft model generation. We imaged human cadaveric proximal femurs at an isotropic resolution of 0.03 mm using a high resolution peripheral quantitative computed tomography (HR-pQCT) scanner. These images, of the Digital Imaging and Communications in Medicine (DICOM) format, were then processed through two methods. In each method, slices and regions of print were selected, filtered to generate a smoothed image, and thresholded. In the conventional method, these processed images are converted to the STereoLithography (STL) format and then resliced to generate G-Code. In the new, direct method, these processed images are run through our computer program and directly converted to G-Code. File size, processing time, and print time were measured for each.

We found that this new method produced a significant reduction in G-Code file size as well as processing time (more than 90% reduction). This allows for more rapid 3D printing from multi-dimensional images.

Purpose

Medical imaging allows generation of volumetric computer models that can be 3D printed. However, due to historic reasons, generation of the instruction set understood by 3D printers (i.e., G-Code) requires substantial user interaction and image manipulations. This process can take a significant amount of time depending on the type of images and application. Furthermore, during the conventional image-based G-Code generation process, some anatomical information could be lost due to surface rendition followed by re-slicing. We developed a method for rapid 3D printing from medical images such as MRI and CT by directly converting 3D image information into G-Code.

As an initial application, here we present data on how patient-specific models can be rapidly 3D printed. Tissue engineering has recently emerged as a promising substitute for autologous and allopathic grafts. The process involves cell proliferation on a biocompatible and biodegradable model followed by reimplantation. Cell sources include autologous or allogeneic cells and mesenchymal stem cells. The major challenge is creating a graft with sufficient mechanical stability that possesses good osteoconductive, osteoinductive, and osteogenic properties.

We present polycaprolactone (PCL) as a promising material for synthetic grafts. PCL degrades in physiological conditions, through hydrolysis of its ester linkages, slower than other biopolymers such as PGA and PLA, making it ideal for construction of long-term degradable implants. Its low melting point (60° C.) allows for easy manufacturing and manipulation into various implants, making PCL a very compatible material for extrusion-based 3D printing [1].

After a patient is scanned, the images have to be processed into 3D printable instructions. We investigated different processes for producing these G-Code instructions for 3D printed modeling through high resolution imaging and extrusion based printing.

Method

To investigate 3D printing from high-resolution imaging, thirteen human cadaveric proximal femurs were selected for this study. The specimens contained seven female and six male, with ages ranging from 36-99. The femurs were imaged at a 0.03 mm isotropic voxel size using a high resolution peripheral quantitative computed tomography (HR-pQCT) scanner and stored as Digital Imaging and Communications in Medicine (DICOM) image files. The resultant DICOM files need to be converted to a format compatible with the 3D printer. Two methods were successful in converting the original DICOM images into 3D printable G-Code instructions. Furthermore, to investigate 3D printing from clinical resolution imaging, we 3D printed human skulls from clinical CT scans.

Conventional Method

First, original DICOM files were converted into the STereoLithography (STL) file format. Next, the CT images were used to select the desired slices and region. The image undergoes 3D Gaussian filtering (sigma=2.50) to generate a smoothed image. Lastly, the images are thresholded to make them binary, and converted to an STL file. The STL file is subsequently transformed into a G-Code file, which allows us to customize our G-Code, making any changes to layer thickness, print path, print angle, etc. For the purposes of this study, layer thickness was set to 0.1 mm. A simple script was created to condense all the steps for DICOM to STL file conversion into a single step to significantly reduce the time required for image processing and output generation.

Direct Method

Our novel method involves a computer program that converts DICOM to G-Code without going through STL. The DICOM images, though, still need to be processed and converted to binary, for which a batch script was also written. This program takes parameters including the printer's resolution, speed of the extruder, etc. The code also allows for choosing the method of printing, from linear, to any inputted angle rotation between each layer. The output is a G-Code file that is then loaded and printed from the 3D bioprinter. In this study, all prints were performed at a 90 degree angle.

Several tests were performed to analyze the advantages and disadvantages of each method. These consisted of tests for time taken to generate the G-Code, print time, and finally print quality. Time to generate G-Code was tested for several samples up to 1000 images, while print time was recorded for prints of ten layers, five layers, and two layers due to time limitations.

FIG. 1 is a flow chart indicating the paths of both the conventional and direct methods.

3D-Printing

We utilized a desktop 3D bioprinter to construct all of our models. A single extruder was loaded with PCL and heated to 100° C. to allow for sufficient melting, and set to a pressure of 100 PSI with an air compressor. In both methods, a 27 gauge nozzle was used with an opening size of 0.2 mm, limiting the resolution to 200 microns. The layer height was set at 0.1 mm. We used circular acrylic glass slides covered with double-sided tape to allow for proper adhesion of the PCL.

Results

Figures 2A, 2B, 2C:
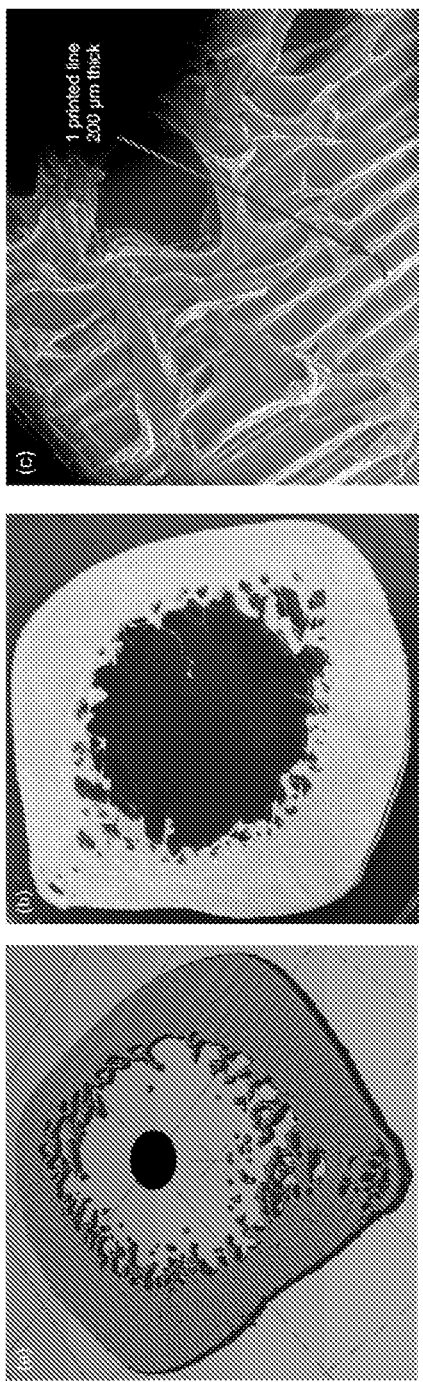
FIG. 2A shows an image of a 5-layer print as an STL.
FIG. 2B shows an example of a printed model.
FIG. 2C shows a scanning electron microscope image of a section of the print.

FIGS. 2A-C illustrate some results from the study. FIG. 2A shows an image of a 5-layer print as an STL. FIG. 2B shows the actual printed model using the conventional method. FIG. 2C shows a scanning electron microscope image of a section of the print.

Table 1 shows that there was a significant reduction in pre-print preparation time, while file size was reduced by an average of 69.96% in the direct method.

TABLE 1

|  | # of layers | Conventional Method | Direct Method |
| --- | --- | --- | --- |
| G-Code File Size | 2 | 491 kb | 137.2 kb |
|  | 5 | 1,120 kb | 347.7 kb |
|  | 10 | 2,159 kb | 672.0 kb |
| Pre-Print Preparation Time | 2 | 4 m 39 s | 0.71 s |
|  | 5 | 7 m 12 s | 1.00 s |
|  | 10 | 14 m 10 s | 1.26 s |

Figure 3:
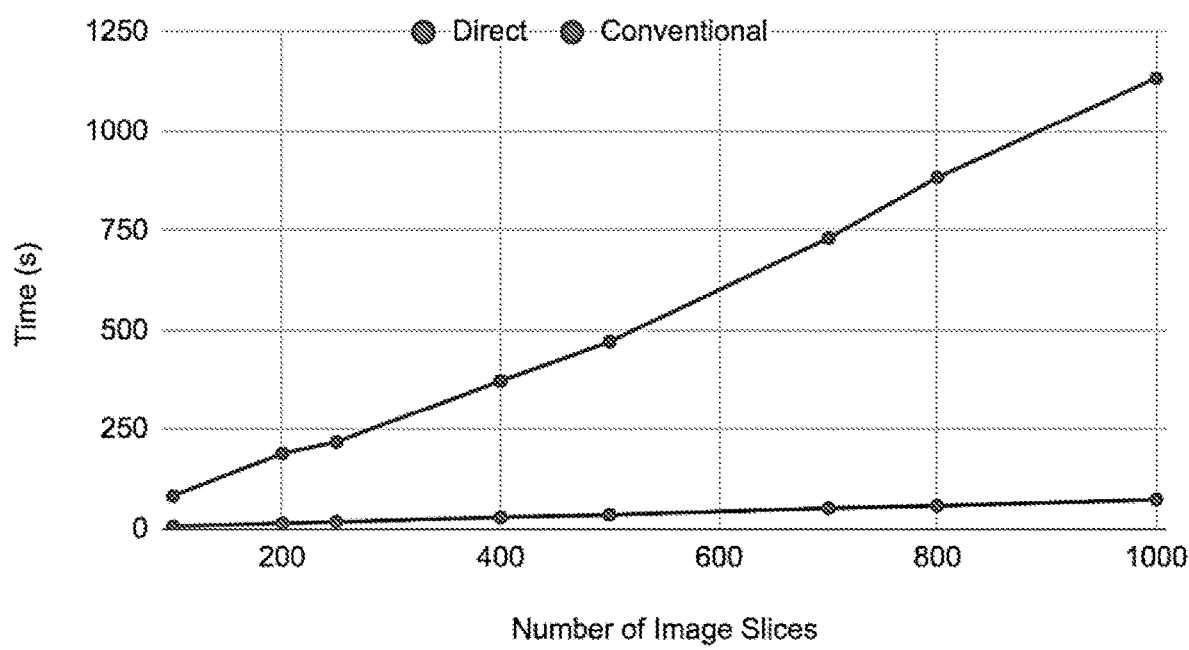
FIG. 3 shows a graph of processing time measured by time taken.

FIG. 3 shows a graph of processing time measured by time taken to run the batch script for each method. The graph shows a linear relationship between number of slices and time for both methods. The processing time for the direct method was an average of 92.23% less than that of the conventional method.

Figure 4:
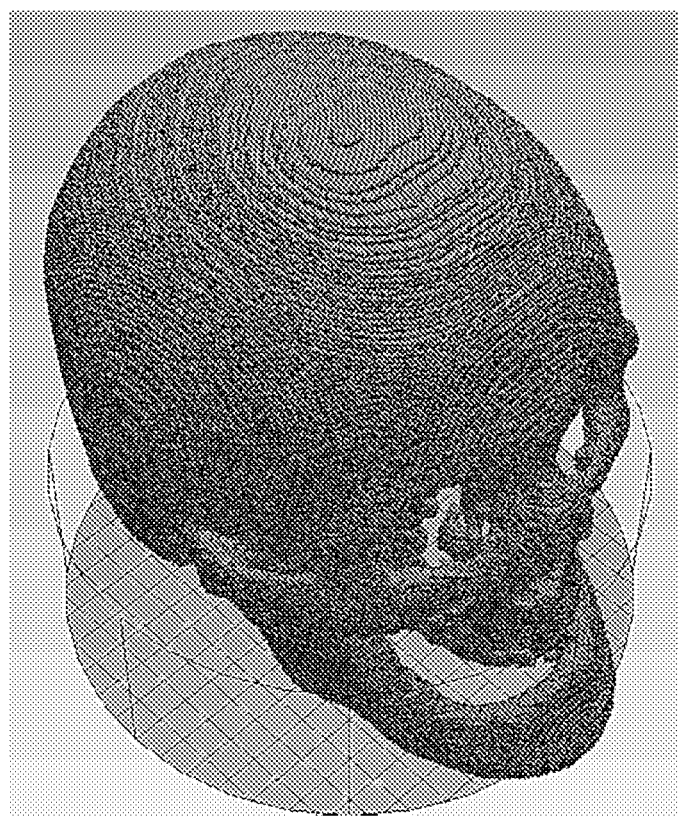
FIG. 4 illustrates a model of G-Code generated for clinical resolution CT scan interpolated to an isotropic resolution of 1 mm.

FIG. 4 illustrates a model of G-Code generated for clinical resolution CT scan interpolated to an isotropic resolution of 1 mm. Produced by the direct method. Conventional method did not work because the image was too big to be resliced.

Breakthroughs

The new method for file conversion resulted in significantly smaller file sizes and shorter processing times, while maintaining comparable print times.

Conventional G-Code generation software typically has a file size limit of approximately 1 Gb, so any STL file larger than 1 Gb could not be converted into G-Code using our conventional method. This limited the number of layers we could print to around 10, because the CT scans used were of such high resolution. On the other hand, the computer program handled 1000 (30 micron resolution) images, which converts to 303 layers, with relative ease, converting the DICOM to G-Code in less than half a minute. Similarly, while typical software could not often handle the re-slicing of the clinical resolution skull, the computer program generated the G-Code in a couple minutes.

CONCLUSION

This study introduced a novel method of directly converting DICOM images from a CT or MRI into the G-Code instructions interpreted by a 3D printer. This approach could substantially reduce the time between a patient taking a scan and obtaining a 3D print from the images. Furthermore, this new program allows for significant improvements in potential for customizability, from changing print speeds in the middle of a print to allowing for different extrusion amounts for either increased porosity or better adhesion. This makes bio printing for medical purposes more feasible and efficient.

Figure 5:
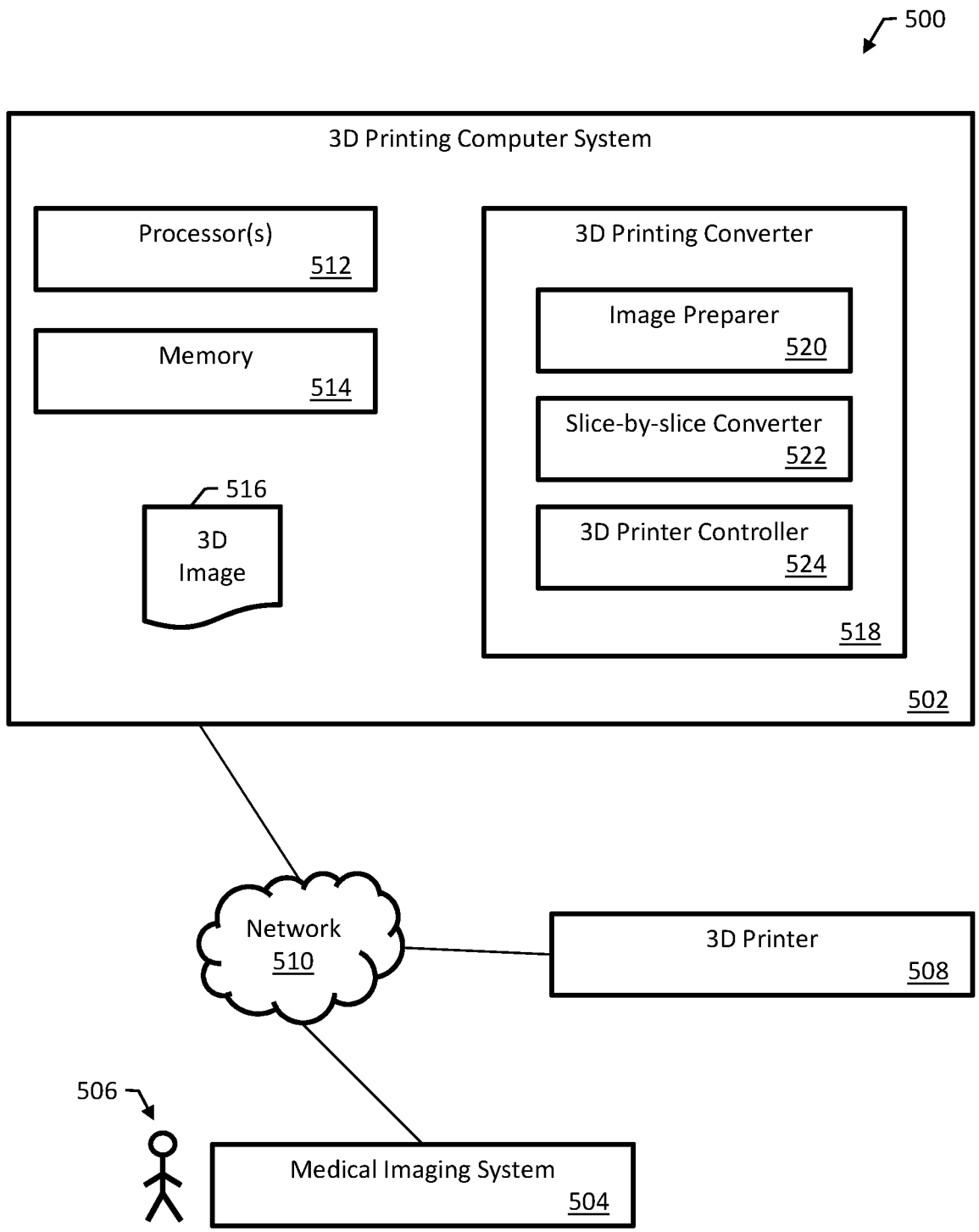
FIG. 5 is a block diagram of an example system for 3D printing from medical images.

FIG. 5 is a block diagram of an example system 500 for 3D printing from medical images. The system 500 includes a 3D printing computer system 502, a medical imaging system 504 configured to image a patient 506, and a 3D printer 508. The computer system 502, medical imaging system 504, and 3D printer 508 can communicate using any appropriate technology, e.g., over a digital communications network 510.

The computer system 502 includes at least one processor 512 and memory 514 storing executable instructions for the processor 512. The computer system 502 receives a 3D image 516 of a structure in the patient 506 from the medical imaging system 504. For example, receiving the 3D image 516 can include receiving a magnetic resonance (MR) image or a computed tomographic (CT) image of a bone structure of the patient 506.

The computer system 518 includes a 3D printing converter 518 implemented using the processor(s) 512 and memory 514. The 3D printing converter 518 can include an image preparer 520 for preparing the 3D image 516, a slice-by-slice converter 522 for converting the 3D image 516 into 3D printing instructions, and a 3D printer controller 524 for controlling the 3D printer 508.

The image preparer 520 can perform one or more of various appropriate tasks to prepare the 3D image 516 for conversion. For example, the image preparer 520 can be configured for thresholding the 3D image 516 to generate a binary image. The image preparer 520 can be configured for segmenting, from the 3D image 516, a portion of the 3D image 516 depicting the structure. The image preparer 520 can be configured for resampling the 3D image 516 to a resolution compatible with the 3D printer 508.

The slice-by-slice converter 522 is configured to, for each two dimensional (2D) slice of the 3D image 516, to convert, row-by-row for each row of the 2D slice, voxels of the 2D slice into 3D printing instructions for the 2D slice. Converting voxels of each 2D slice into 3D printing instructions can include converting intensity data in the 3D image to density instructions for 3D printing. As a result, the 3D printer controller 524 can use the 3D printer 508 for variable density printing.

The 3D printer controller 524 is configured for 3D printing, using the 3D printer 508, a model based on the structure by 3D printing, slice by slice, each 2D slice using the 3D printing instructions. In some examples, the 3D printer 508 is a 3D printing extruder. Converting voxels of each 2D slice into 3D printing instructions can include specifying, for the 3D printing extruder, an extrusion direction or extrusion angle or both for the 2D slice. Converting voxels of each 2D slice into 3D printing instructions can include specifying, for the 3D printing extruder, an extrusion speed or extrusion temperature or both for the 2D slice.

Figure 6:
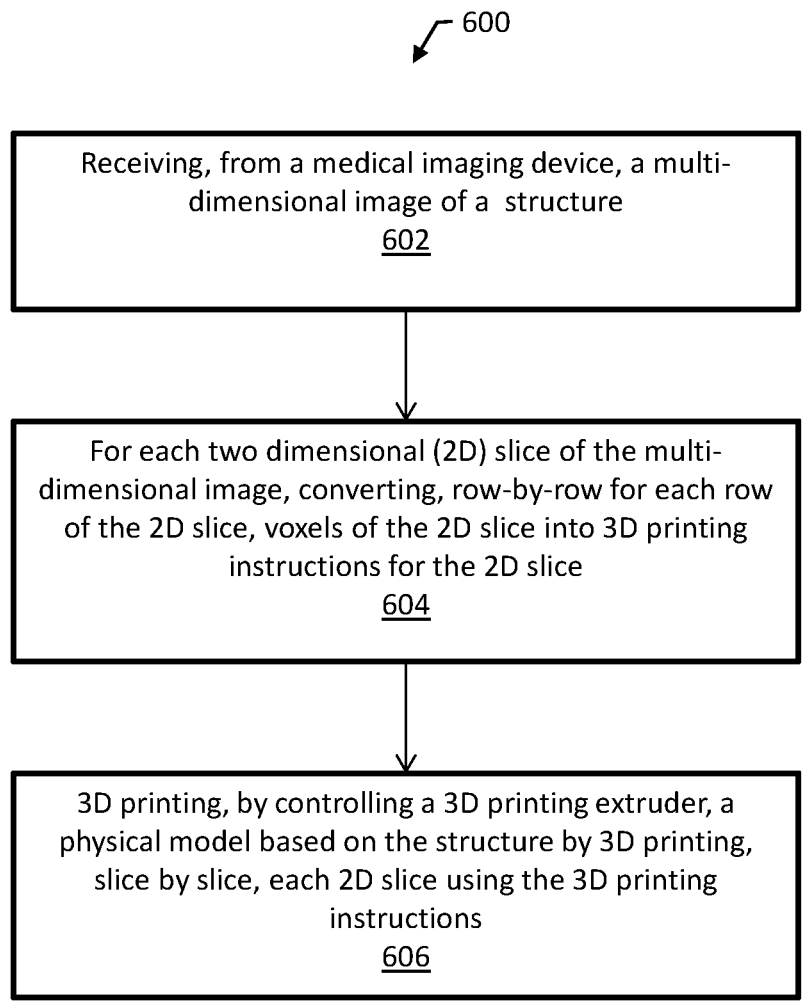
FIG. 6 is a flow chart of an example method for 3D printing from medical images.

FIG. 6 is a flow diagram of an example method 600 for 3D printing from medical images. The method includes receiving, from a medical imaging device, a multi-dimensional image of a structure (602). The multi-dimensional image may be an original image of the structure or a modified image of the structure. For example, the multi-dimensional image may be a re-sampled image that was re-sampled from an original image. The method includes, for each two dimensional (2D) slice of the multi-dimensional image, converting, row-by-row for each row of the 2D slice, voxels of the 2D slice into 3D printing instructions for the 2D slice (604). The method includes 3D printing, by controlling a 3D printing extruder, a physical model based on the structure by 3D printing, slice by slice, each 2D slice using the 3D printing instructions (606).

Although specific examples and features have been described above, these examples and features are not intended to limit the scope of the present disclosure, even where only a single example is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed in this specification (either explicitly or implicitly), or any generalization of features disclosed, whether or not such features or generalizations mitigate any or all of the problems described in this specification. Accordingly, new claims may be formulated during prosecution of this application (or an application claiming priority to this application) to any such combination of features. In particular, with reference to the appended claims, features from dependent claims may be combined with those of the independent claims and features from respective independent claims may be combined in any appropriate manner and not merely in the specific combinations enumerated in the appended claims.

REFERENCES

The disclosure of each of the following references is incorporated herein by reference in its entirety.
1. Tokiwa Y, Calabia B P, Ugwu C U, Aiba S. Biodegradability of Plastics. *International Journal of Molecular Sciences.* 2009; 10(9):3722-3742. doi:10.3390/ijms10093722.
2. Grevera G, Udupa J, Odhner D, et al. CAVASS: A Computer-Assisted Visualization and Analysis Software System. *Journal of Digital Imaging.* 2007; 20(Suppl 1):101-118. doi:10.1007/s10278-007-9060-5.

What is claimed is:
1. A method for 3D printing from multi-dimensional images, the method comprising:
   receiving at least one multi-dimensional image of a structure, wherein receiving the multi-dimensional image of the structure comprises receiving a magnetic resonance (MR) image or a computed tomography (CT) image of a structure of a patient, wherein receiving the multi-dimensional image of the structure comprises pre-processing the multi-dimensional image to generate a binary image;
   for each two dimensional (2D) slice of a plurality of 2D slices of the multi-dimensional image, converting, row-by-row for each row of a plurality of rows of the 2D slice, voxels of the 2D slice into 3D printing instructions for the 2D slice, wherein converting voxels of each 2D slice into 3D printing instructions comprises converting visual image intensity data in the MR image or CT image of the structure of the patient to structural density information for 3D printing, wherein the structural density information for 3D printing specifies that different regions of the 2D slice have different levels of structural material density; and 3D printing a physical model based on the structure by 3D printing, slice by slice, each 2D slice using the 3D printing instructions, including performing variable density printing using the structural density information.

2. The method of claim 1, wherein receiving the multi-dimensional image of the structure comprises segmenting, from the multi-dimensional image, a portion of the multi-dimensional image depicting the structure.

3. The method of claim 1, wherein receiving the multi-dimensional image of the structure comprises resampling the multi-dimensional image to a resolution compatible with a 3D printer.

4. The method of claim 1, wherein 3D printing the physical model comprises using at least one 3D printing extruder.

5. The method of claim 4, wherein converting voxels of each 2D slice into 3D printing instructions comprises specifying, for the 3D printing extruder, an extrusion direction or extrusion angle or both for the 2D slice.

6. The method of claim 4, wherein converting voxels of each 2D slice into 3D printing instructions comprises specifying, for the 3D printing extruder, an extrusion speed or extrusion temperature or both for each print segment of a plurality of print segments.

7. The method of claim 1, wherein 3D printing the physical model comprises controlling a plurality of extruders to each cover a respective portion of each 2D slice using a respective material for the portion.

8. The method of claim 1, wherein 3D printing the physical model comprises altering, while printing at least one segment of at least one 2D slice, one or more of: speed, density, porosity, adhesion, and gap distance between print locations.

9. A system for 3D printing from multi-dimensional images, the system comprising:
   at least one processor; and
   a 3D printing converter implemented on the at least one processor and configured to perform operations comprising:
      receiving at least one multi-dimensional image of a structure, wherein receiving the multi-dimensional image of the structure comprises receiving a magnetic resonance (MR) image or a computed tomographic (CT) image of a structure of a patient, wherein receiving the multi-dimensional image of the structure comprises pre-processing the multi-dimensional image to generate a binary image;
      for each two dimensional (2D) slice of a plurality of 2D slices of the multi-dimensional image, converting, row-by-row for each row of a plurality of rows of the 2D slice, voxels of the 2D slice into 3D printing instructions for the 2D slice, wherein converting voxels of each 2D slice into 3D printing instructions comprises converting visual image intensity data in the MR image or CT image of the structure of the patient to structural density information for 3D printing, wherein the structural density information for 3D printing specifies that different regions of the 2D slice have different levels of structural material density; and
      3D printing a physical model based on the structure by 3D printing, slice by slice, each 2D slice using the 3D printing instructions, including performing variable density printing using the structural density information.

10. The system of claim 9, wherein receiving the multi-dimensional image of the structure comprises segmenting, from the multi-dimensional image, a portion of the multi-dimensional image depicting the structure.

11. The system of claim 9, wherein receiving the multi-dimensional image of the structure comprises resampling the multi-dimensional image to a resolution compatible with a 3D printer.

12. The system of claim 9, wherein 3D printing the physical model comprises using at least one 3D printing extruder.

13. The system of claim 12, wherein converting voxels of each 2D slice into 3D printing instructions comprises specifying, for the 3D printing extruder, an extrusion direction or extrusion angle or both for the 2D slice.

14. The system of claim 12, wherein converting voxels of each 2D slice into 3D printing instructions comprises specifying, for the 3D printing extruder, an extrusion speed or extrusion temperature or both for each print segment of a plurality of print segments.

15. The system of claim 9, wherein 3D printing the physical model comprises controlling a plurality of extruders to each cover a respective portion of each 2D slice using a respective material for the portion.

16. The system of claim 9, wherein 3D printing the physical model comprises altering, while printing at least one segment of at least one 2D slice, one or more of: speed, density, porosity, adhesion, and gap distance between print locations.

17. A non-transitory computer readable medium storing executable instructions that when executed by at least one processor of a computer control the computer to perform operations comprising:
   receiving at least one multi-dimensional image of a structure, wherein receiving the multi-dimensional image of the structure comprises receiving a magnetic resonance (MR) image or a computed tomographic (CT) image of a structure of a patient, wherein receiving the multi-dimensional image of the structure comprises pre-processing the multi-dimensional image to generate a binary image;
   for each two dimensional (2D) slice of a plurality of 2D slices of the multi-dimensional image, converting, row-by-row for each row of a plurality of rows of the 2D slice, voxels of the 2D slice into 3D printing instructions for the 2D slice, wherein converting voxels of each 2D slice into 3D printing instructions comprises converting visual image intensity data in the MR image or CT image of the structure of the patient to structural density information for 3D printing, wherein the structural density information for 3D printing specifies that different regions of the 2D slice have different levels of structural material density; and
   3D printing a physical model based on the structure by 3D printing, slice by slice, each 2D slice using the 3D printing instructions, including performing variable density printing using the structural density information.

18. A system for 3D printing from multi-dimensional images, the system comprising:
   a medical imaging device;
   at least one 3D printing extruder; and
   a computer system programmed for:

receiving, from the medical imaging device, a multi-dimensional image of a structure, wherein receiving the multi-dimensional image of the structure comprises receiving a magnetic resonance (MR) image or a computed tomographic (CT) image of a structure of a patient, wherein receiving the multi-dimensional image of the structure comprises pre-processing the multi-dimensional image to generate a binary image;

for each two dimensional (2D) slice of a plurality of 2D slices of the multi-dimensional image, converting, row-by-row for each row of a plurality of rows of the 2D slice, voxels of the 2D slice into 3D printing instructions for the 2D slice, wherein converting voxels of each 2D slice into 3D printing instructions comprises converting visual image intensity data in the MR image or CT image of the structure of the patient to structural density information for 3D printing, wherein the structural density information for 3D printing specifies that different regions of the 2D slice have different levels of structural material density; and 3D printing, by controlling the 3D printing extruder, a physical model based on the structure by 3D printing, slice by slice, each 2D slice using the 3D printing instructions, including performing variable density printing using the structural density information.

* * * * *

UNITED STATES PATENT AND TRADEMARK OFFICE
CERTIFICATE OF CORRECTION

| | |
|---|---|
| PATENT NO. | : 11,872,764 B2 |
| APPLICATION NO. | : 16/768645 |
| DATED | : January 16, 2024 |
| INVENTOR(S) | : Chamith Sudesh Rajapakse |

It is certified that error appears in the above-identified patent and that said Letters Patent is hereby corrected as shown below:

On the Title Page

Item (73) (Assignee):
Replace "UNIVERISTY"
With --"UNIVERSITY"--.

Signed and Sealed this
Fifth Day of March, 2024

*Katherine Kelly Vidal*
*Director of the United States Patent and Trademark Office*